US011278348B2

(12) United States Patent
Son et al.

(10) Patent No.: US 11,278,348 B2
(45) Date of Patent: Mar. 22, 2022

(54) HIGH-FREQUENCY TREATMENT DEVICE FOR ENDOSCOPIC SPINAL SURGERY

(71) Applicants: ENDOVISION CO., LTD., Daegu (KR); Min Ho Jung, Daegu (KR)

(72) Inventors: Sang-Kyu Son, Busan (KR); Min Ho Jung, Daegu (KR); Mingi Kang, Gumi-si (KR)

(73) Assignees: ENDOVISION CO., LTD., Daegu (KR); Min Ho Jung, Daegu (KR)

( * ) Notice: Subject to any disclaimer, the term of this patent is extended or adjusted under 35 U.S.C. 154(b) by 702 days.

(21) Appl. No.: 15/771,273

(22) PCT Filed: Aug. 8, 2017

(86) PCT No.: PCT/KR2017/008536
§ 371 (c)(1),
(2) Date: Apr. 27, 2018

(87) PCT Pub. No.: WO2018/159908
PCT Pub. Date: Sep. 7, 2018

(65) Prior Publication Data

US 2019/0053843 A1 Feb. 21, 2019

(30) Foreign Application Priority Data

Feb. 28, 2017 (KR) ........................ 10-2017-0026568

(51) Int. Cl.
*A61B 18/12* (2006.01)
*A61B 18/14* (2006.01)
(Continued)

(52) U.S. Cl.
CPC .......... *A61B 18/148* (2013.01); *A61B 5/4566* (2013.01); *A61B 5/4836* (2013.01);
(Continued)

(58) Field of Classification Search
CPC ................ A61B 18/042; A61B 18/148; A61B 2018/00708; A61B 2018/00791; A61B 2018/00839; A61B 2018/00982
See application file for complete search history.

(56) References Cited

U.S. PATENT DOCUMENTS 5,944,715 A * 8/1999 Goble .................. A61B 18/148 606/41
6,176,857 B1 * 1/2001 Ashley .................. A61B 18/08 606/32
(Continued)

FOREIGN PATENT DOCUMENTS

KR 10-2012-0075711 A 7/2012

*Primary Examiner* — Daniel W Fowler
(74) *Attorney, Agent, or Firm* — Stein IP, LLC

(57) ABSTRACT

The present invention relates to a high-frequency treatment device for spinal endoscopic surgery, the device including: a casing; an insert rod extending in a longitudinal direction of the casing; and an electrode tip formed at a front end of the insert rod to apply heat to a treatment part. Accordingly, it is possible to not only immediately remove in-body soft tissues or ligaments that interfere with the visual field of an endoscope in an operation, but quickly stop bleeding, and it is also possible to discharge contaminated substances with a saline solution from a treatment part, thereby allowing an accurate and effective operation.

9 Claims, 5 Drawing Sheets

41
41d 41c 43 43a 41a 41b
29 29a
31

(51) Int. Cl.

| | |
|---|---|
| ***A61B 5/00*** | (2006.01) |
| *A61B 18/00* | (2006.01) |
| *A61B 18/04* | (2006.01) |
| *A61B 5/01* | (2006.01) |
| *A61B 5/11* | (2006.01) |

(52) U.S. Cl.

CPC ............... *A61B 5/01* (2013.01); *A61B 5/1107* (2013.01); *A61B 5/6826* (2013.01); *A61B 18/042* (2013.01); *A61B 2018/0044* (2013.01); *A61B 2018/00708* (2013.01); *A61B 2018/00791* (2013.01); *A61B 2018/00839* (2013.01); *A61B 2018/00982* (2013.01); *A61B 2218/002* (2013.01); *A61B 2218/007* (2013.01); *A61B 2505/05* (2013.01)

(56) References Cited

U.S. PATENT DOCUMENTS

| | | | | |
|---|---|---|---|---|
| 7,611,509 | B2 * | 11/2009 | Van Wyk | A61B 18/1485 606/37 |
| 9,439,715 | B2 * | 9/2016 | Benn | A61B 18/148 |
| 2007/0066971 | A1 * | 3/2007 | Podhajsky | A61N 1/36021 606/34 |
| 2009/0048592 | A1 * | 2/2009 | Thomas | A61B 18/148 606/33 |
| 2010/0081987 | A1 * | 4/2010 | Christian | A61B 18/1492 604/21 |
| 2012/0116261 | A1 * | 5/2012 | Mumaw | A61B 18/12 601/2 |

* cited by examiner

HIGH-FREQUENCY TREATMENT DEVICE FOR ENDOSCOPIC SPINAL SURGERY

CROSS-REFERENCE TO RELATED APPLICATIONS

This application is a national stage of International Application No. PCT/KR2017/008536, filed Aug. 8, 2017, which claims the benefit of priority to Korean Application No. 10-2017-0026568, filed Feb. 28, 2017, in the Korean Intellectual Property Office, the disclosure of which are incorporated herein by reference.

BACKGROUND OF THE INVENTION

Field of the Invention

The present invention relates to a treatment device for spinal surgery and, more particularly, to a high-frequency treatment device for endoscopic spinal surgery, the device being able to immediately remove soft tissues or ligaments that interfere with the visual field of an endoscope in a body in an operation and being able to quickly stop bleeding.

Description of the Related Art

The spine of a human body, which is a bone frame forming the vertebral column, is composed of the cervical vertebrae, the dorsal vertebrae, the lumbar vertebrae, the sacrum formed by combination of sacrals bones, and the coccyx formed by combination of caudal bones. These bones are connected by joints, and intervertebral discs are positioned between the bones. The spine plays an important role including absorbing shock, being a base of motions, and protecting all of the internal organs.

However, when the intervertebral discs connecting the vertebral bodies of the spine are moved from the normal positions due to degeneration or rupture or when joints that are protrusions on the rear of the spine are damaged or degenerated, the roots disposed through the spinal canal are pressed and a pain is caused.

A relatively large part is opened to expose the spine in common spinal operations, so various problems accompany such as severe pain and long time for recovery, and accordingly, recently, minimally invasive surgery has been generally used.

This treatment is a method of percutaneously putting a catheter to a diseased part under local anesthesia and then performing necessary treatment whereby, for example, an intervertebral disc is reduced or fixes or pressure on a root is removed by applying high-frequency heat to the intervertebral disc.

Further, as an example of a minimum invasive surgery, an operation method that secures a space for treatment by opening a cut part to both sides using a pair of expender pipes that can open and close at the lower end using a hinge has been disclosed in Korean Patent Application Publication No. 10-2012-0075711, titled “Minimally operation system for spinal surgical operation”

However, this minimally invasive surgery is merely a single-port endoscopic surgery and can only treat spinal disc herniation, that is, the treatment range is narrow. This method cannot be applied to common operations that are relatively frequently performed such as foraminotomy or operations for spinal canal stenosis, or spondylolisthesis.

In order to overcome this limit, recently, unilateral biportal endoscopy (UBE) has been used. UBE is an operation method wherein two small holes are bored through the skin and a spinal endoscope is inserted into one of the holes and surgical tools into the other hole. UBE can prevent damage to tissues including muscles, causes little inflammation, and particularly, can be used to treat almost all spinal diseases.

The important thing in UBE is to secure an accurate visual field. If the lens at the front end of an endoscope is covered with a tissue or blood in a body, quick and effective treatment is impossible. Various assistant surgical tools for UBE have been developed, but a tool for active assistance such as removing a soft tissue or a ligament to secure the visual field of an endoscope has not been developed yet.

SUMMARY OF THE INVENTION

The present invention has been made in an effort to solve the problems and an object of the present invention is to provide a high-frequency treatment device for endoscopic spinal surgery, the device allowing for an accurate and effective operation because it can immediately remove a soft tissue or a ligament that interferes with the visual field of an endoscope in a body in an operation, it can quickly stop bleeding, and it can discharge contaminants out of the body by sprinkling water to a diseased part.

In order to achieve the objects of the present invention, a high-frequency treatment device for spinal endoscopic surgery includes: a casing; an insert rod extending in a longitudinal direction of the casing; and an electrode tip formed at a front end of the insert rod to apply heat to a treatment part.

The electrode tip may include: a body fitted in the front end of the insert rod and having a passage that communicates with the insert rod; and a heat generator formed on a first side of the body.

A plurality of protrusions for preventing the heat generator and tissue of a human body from sticking to each other may be formed at the heat generator.

A seat for accommodating the heat generator may be formed on the first side of the body and the heat generator may be disposed inside the seat and is operated with the protrusions exposed outside.

Holes that communicate with the passage of the body may be further formed at the heat generator.

A shield for isolating the heat generator from a human tissue may be further formed on a second side of the body.

The high-frequency treatment device may further include a discharge tube for discharging a saline solution, which is injected to a treatment part in a human body from the outside, to the outside of the human body through the holes, the passage, and the insert rod.

The casing may have a trigger at a side to operate the electrode tip.

The insert rod is formed in a hollow pipe shape coated with an insulating material on an outer side thereof or having an insulating coating on the outer side.

A high-frequency output unit operated to output high frequency waves by power supplied from the outside may be disposed in the casing and energy generated by the high-frequency output unit may be transmitted to the electrode tip.

A switch unit operating the high-frequency output unit may be further disposed in the casing, and the high-frequency treatment device may further include: a sensing unit determining suitability of temperature of tissues in a treatment part; and a controller turning on and off the switch unit in response to information sensed by the sensing unit, in which the sensing unit and the controller may be installed with the electrode tip.

The sensing unit may include an in-body sensor inserted into a human body in an operation and may include an out-body sensor fastened on a finger or a toe of a patient to sense a nerve reaction of the finger or the toe.

According to a high-frequency treatment device for endoscopic spinal surgery of the present invention, it is possible to not only immediately remove in-body soft tissues or ligaments that interfere with the visual field of an endoscope in an operation, but quickly stop bleeding, and it is also possible to discharge contaminated substances with a saline solution from a treatment part,

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Embodiments of the present invention will be described hereafter in detail with reference to the accompanying drawings.

Figure 1:
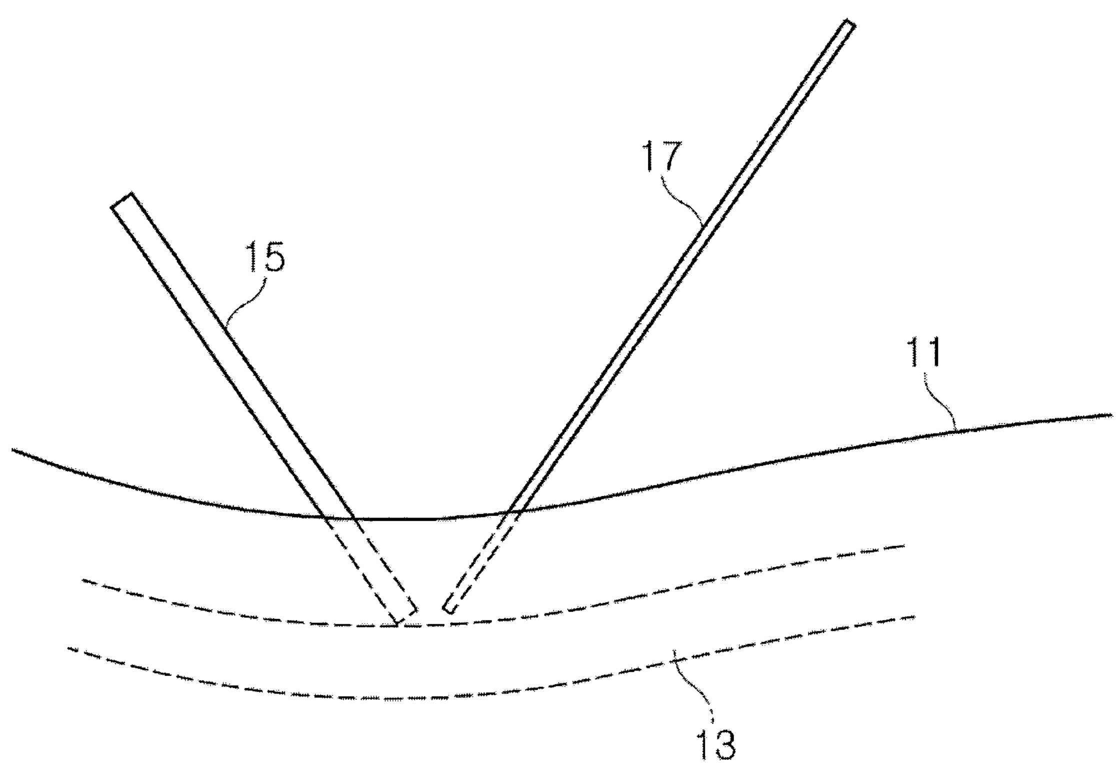
FIG. 1 is a view illustrating the basic concept of UBE to which the high-frequency treatment device for endoscopic spinal surgery according to the present invention is applied.
Figure 2:
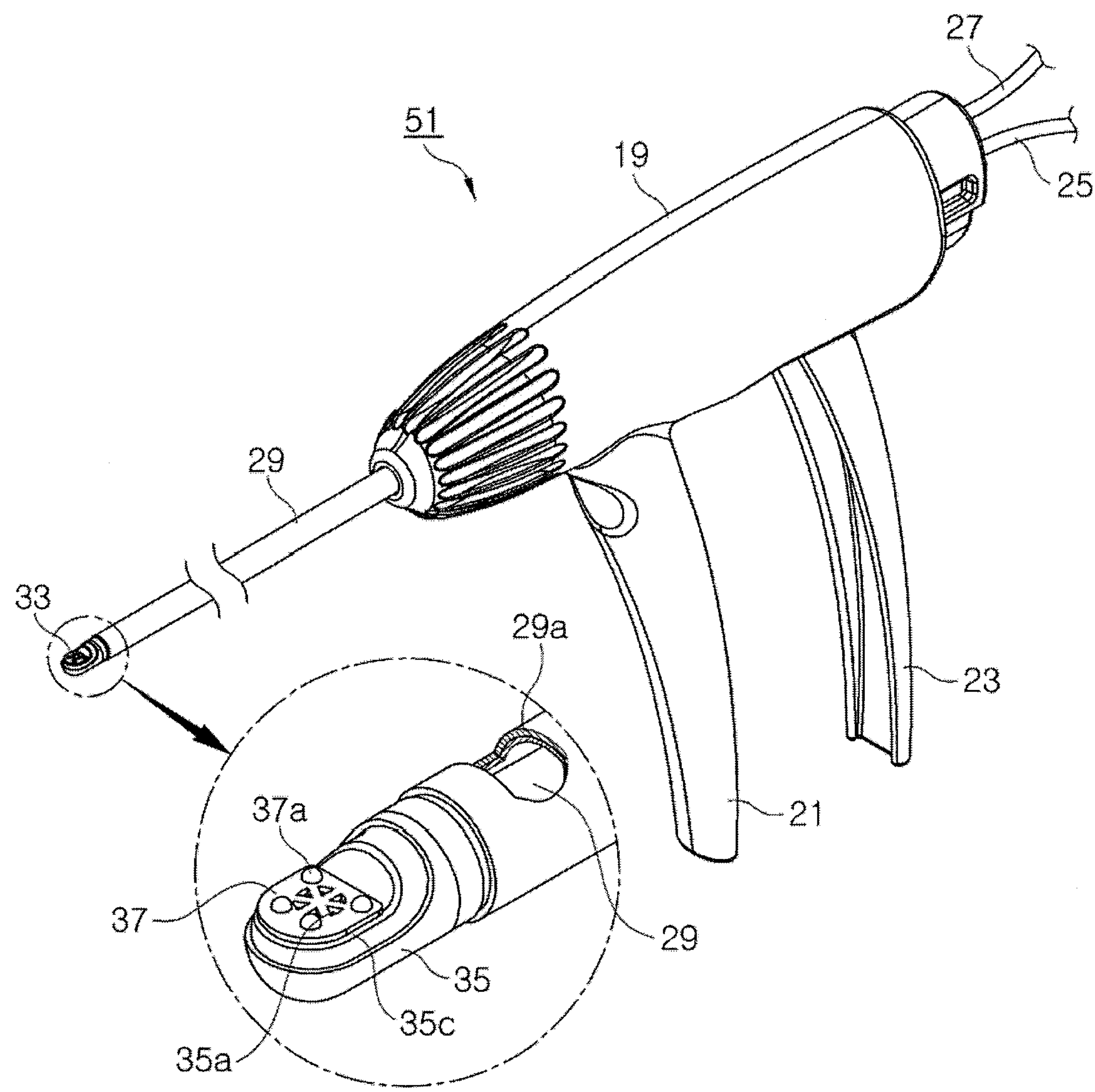
FIG. 2 is a partial cut perspective view showing the structure of a high-frequency treatment device for endoscopic spinal surgery according to a first embodiment of the present invention.
Figure 3:
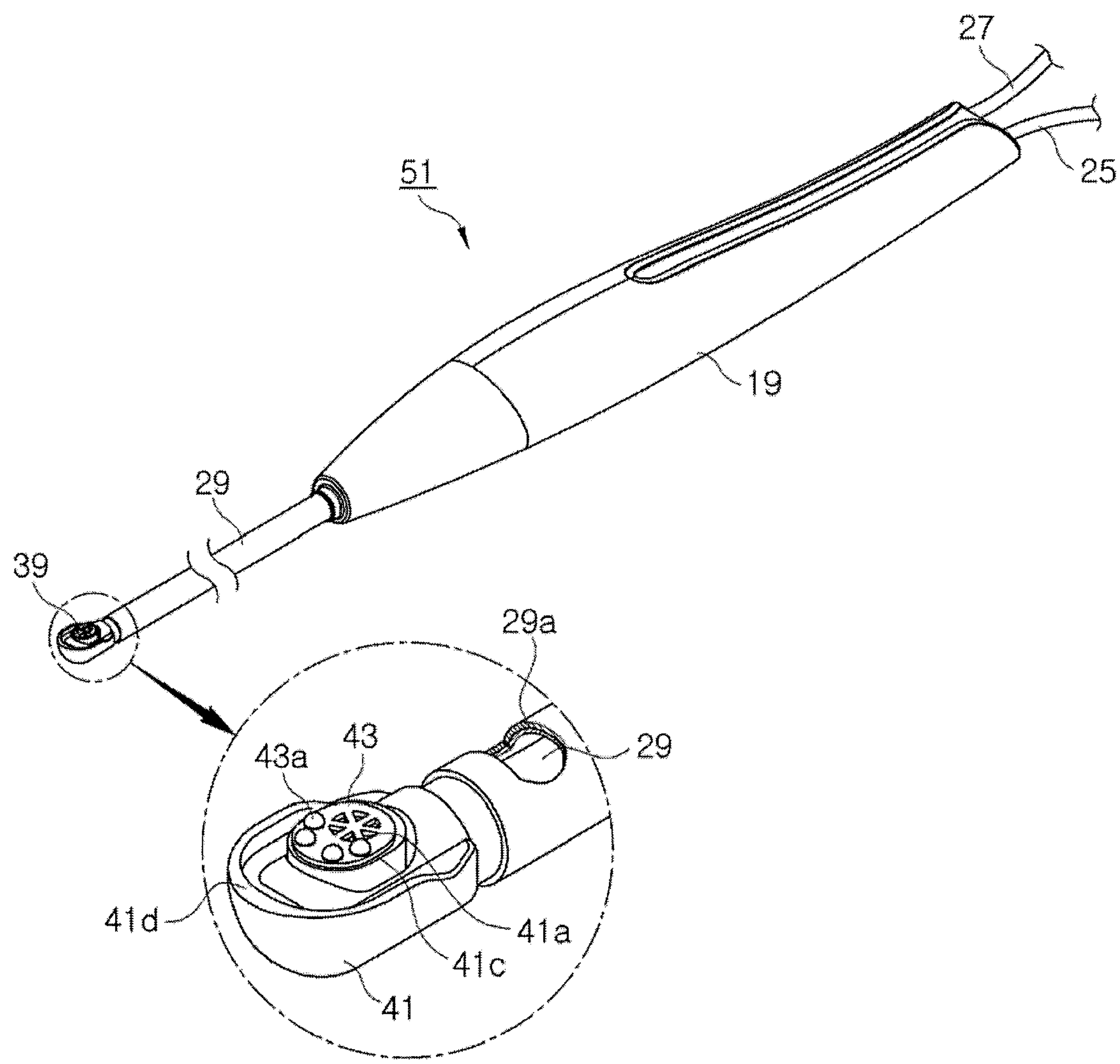
FIG. 3 is a partial cut perspective view showing the structure of a high-frequency treatment device for endoscopic spinal surgery according to a second embodiment of the present invention.
Figure 4:
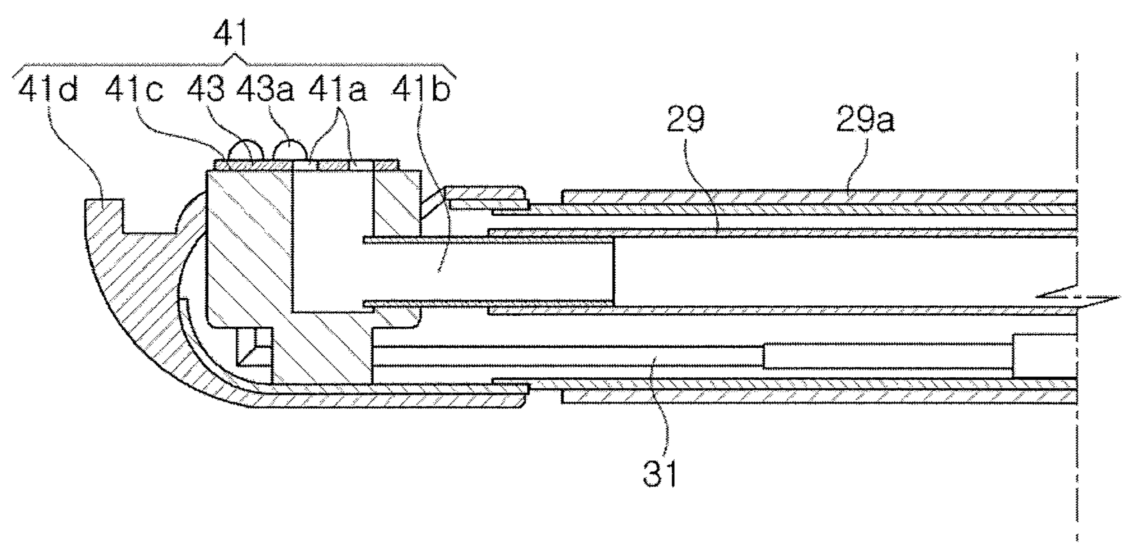
FIG. 4 is a cross-sectional view of an electrode tip of the high-frequency treatment device for endoscopic spinal surgery according to the second embodiment of the present invention.
Figure 5:
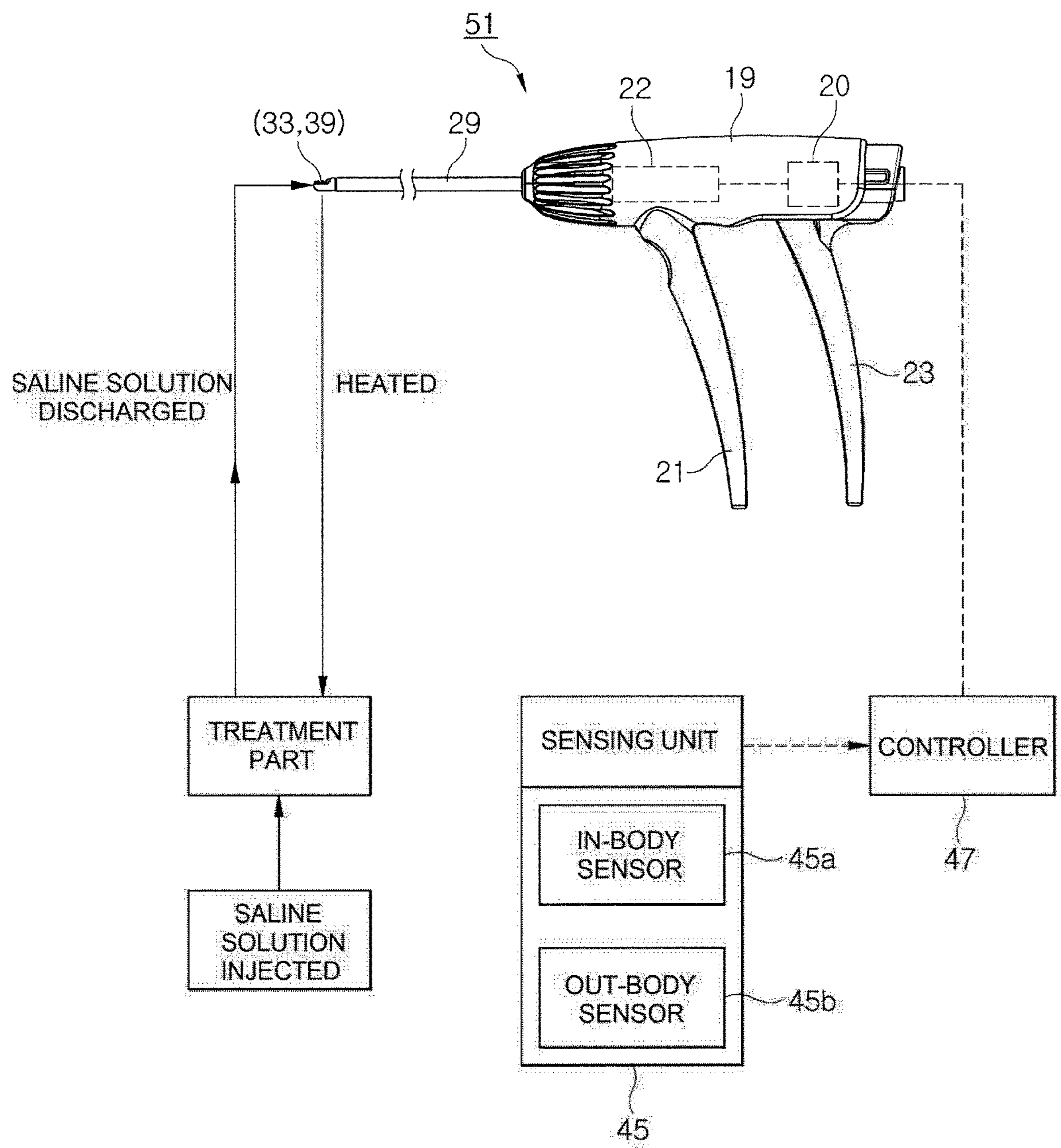
FIG. 5 is a view illustrating the operation of the electrode tip of the high-frequency treatment device for endoscopic spinal surgery according to the second embodiment of the present invention.

FIG. 1 is a view illustrating the basic concept of UBE to which the high-frequency treatment device for endoscopic spinal surgery according to the present invention is applied, FIG. 2 is a partial cut perspective view showing the structure of a high-frequency treatment device for endoscopic spinal surgery according to a first embodiment of the present invention, FIG. 3 is a partial cut perspective view showing the structure of a high-frequency treatment device for endoscopic spinal surgery according to a second embodiment of the present invention, FIG. 4 is a cross-sectional view of an electrode tip of the high-frequency treatment device for endoscopic spinal surgery according to the second embodiment of the present invention, and FIG. 5 is a view illustrating the operation of the electrode tip of the high-frequency treatment device for endoscopic spinal surgery according to the second embodiment of the present invention.

Fundamentally, a high-frequency treatment device for endoscopic spinal surgery according to an embodiment of the present invention can be used for not only single-port spinal endoscopy, but UBE as stated above.

In single-port spinal endoscopy, an endoscope is inserted into a port and a high-frequency treatment device for spinal endoscopy according to the present invention is inserted into a separate hole in the endoscope. Accordingly, the diameters of ports are fixed, so the outer diameters of electrode tips and insert rods are limited. Therefore, the present invention was designed to have shapes and structures of an electrode tip and an insert rod that have maximum areas within the limit.

Further, according to UBE, two ports are formed, an endoscope is inserted into one of the ports and a tool kit or the high-frequency treatment device for a spinal endoscopic surgery according to the present invention is inserted into the other port with a specific passage or trocar, so the limits in diameter of an electrode tip and insert rod are attenuated. Accordingly, for example, it may be important technological characteristics to be able to increase the size of a heating unit that generates high-frequency heat or to apply a shield that can prevent thermal conduction to roots etc.

UBE can further increase an operation effect by being used with other surgical tools such as an endoscope. For example, a clear visual field is provided to prevent damage to surrounding roots or bleeding is quickly stopped.

FIG. 1 is a view schematically illustrating the basic concept of UBE to which the high-frequency treatment device for endoscopic spinal surgery according to the present invention is applied.

As shown in the figure, it can be seen that an endoscope 15 and a high-frequency treater 17 are inserted toward the spine of a patient 11 lying prostrate. The surgical method of inserting two surgical tools into the body of a patient is UBE.

The high-frequency treater 17, which is a part of a high-frequency treatment device 51 (see FIG. 5), for example, removes a soft tissue or a ligament or stops bleeding or discharges contaminated blood or body fluid to the outside by applying high-frequency heat to tissues with the front end reaching the target in the body.

FIG. 2 is a partial cut perspective view of the high-frequency treatment device 51 for endoscopic spinal surgery according to a first embodiment of the present invention. In particular, the high-frequency treatment device 51 of FIG. 2 is suitable for a single-port spinal endoscopic surgery, but may be used for UBE.

As shown in the figure, the high-frequency treatment device 51 largely includes a casing 19, an insert rod 29 extending in the longitudinal direction of the case 19, and an electrode tip 33 formed at the front end of the insert rod 29 to apply heat to a diseased part.

In detail, the high-frequency treatment device 51 fundamentally includes the casing 19 having a handle and a trigger 23, a switch unit 20 (see FIG. 5) and a high-frequency output unit 22 (see FIG. 22) disposed in the casing 19, the insert rod 29 longitudinally extending with an end fixed to the casing, and the electrode tip 33 disposed at the extended end of the insert rod 29.

The casing 19 is the part that a doctor carries in an operation and, for example, a doctor can push the trigger 23 forward with a palm with fingers on the handle 21. When the trigger 23 is pushed forward, the electrode tip 33 is operated to generate heat.

A power line 25 may be connected to the outer side of the casing 19. The power line 25 is provided to apply power from an external power supply to the high-frequency output unit 22. The high-frequency output unit 22 is powered through the power line 25, thereby outputting high-frequency energy. The energy output from the high-frequency output unit 22 is transmitted to a heat generator 37 through a supply line 31 in the insert rod 29. The heat generator 37 generates heat by receiving the high-frequency energy, thereby heating surrounding tissues.

The switch unit 20 functions as a switch that turns on and off the high-frequency output unit 22. For example, as will be described below, it is possible to stop the operation of the high-frequency output unit 22 in response to a stop signal from a controller 27. When the controller 47 transmits a restart signal, the high-frequency output unit 22 is restarted. The method of turning on and off the high-frequency output unit 22 through the switch unit 20 may be achieved in various ways.

A discharge tube 27 may extend out of the casing 19 to discharge a saline solution injected to the treatment part inside a body from the outside to the outside of the body through the insert rod 29.

That is, the discharge tube 27 is a flexible tube for discharging contaminated body fluid, blood, or fragments of tissues in a body to the outside of the body in suction and communicates with the rear end of the insert rod 29 in the casing 19.

Accordingly, for example, when vacuum pressure is applied to the discharge tube 27, surrounding objects to be removed, for example, pieces of bones or contaminated body fluid are suctioned into the insert rod 29 through holes 31*a* and a passage formed at the electrode tip 33 at the front end of the insert rod 29, whereby the objects can be discharged outside through the discharge tube 27.

The insert rod 29 is a hollow pipe-shaped member longitudinally extending, and particularly, is coated with Teflon tape that is an insulating material on the outside of an insulating coating 29*a* such as PVDF is formed on the outer side. In some cases, an insulating material similar to Teflon tape or PVDF may be used.

A channel connecting the passage and the discharge tube 27 to each other is formed in the insert rod 29. The channel is a way to guide the substances suctioned into the passage to the discharge tube 27.

A shape memory wire (not shown) may be disposed in the insert rod 29. That is, a shape memory wire that is bent in a designed direction in an operation is disposed in the insert rod 29. Since a shape memory wire is provided, it is possible to more easily put the front end of the insert rod 29, that is, the electrode tip 33 close to a treatment part.

The electrode tip 33 is composed of a body 35 fitted in the front end of the insert rod 29 and a heat generator 37 fixed to a side of the body 35. The body 35 has a substantially cylindrical shape, which was designed in consideration of ease and efficiency of operation.

The body 35 is made of a ceramic material by forming and has holes 35*a* at the upper portion of the center portion and a passage that communicates with the holes 35*a* in the center portion. The holes 35*a* are holes formed through the body 35 and having a predetermined diameter and the passage connects the holes 35*a* and the channel in the insert rod 29 to each other, so when vacuum pressure is applied to the discharge tube 27, surrounding objects are suctioned into the holes, as described above.

The surrounding objects are contaminated body fluid or blood or separated pieces or powder of bones. Further, the passage is also a way through which a saline solution injected to a treatment body is discharged to secure a visual field for the operation part, which will be described below.

A seat 35*c* is formed on a side of the body 35. The seat 35*c* is a groove or a plate provided for accommodating the heat generator 37 therein, and particularly, provides a contact way for contact between the heat generator 37 and the supply line 31. By the contact way, the heat generator 37 is in contact with the supply line 31 and receives high-frequency energy.

The heat generator 27, which is a part generating heat by receiving high-frequency energy, is disposed in the seat 35*c* to be partially exposed and outputs heat of 40° C. to 75° C. The heat generator 37 is made of tungsten. However, it may be made of stainless steel in some cases. The heat output from the heat generator 37 is used to melting and removing surrounding soft tissues or ligamentum flavum.

A plurality of protrusions 37*a* is formed on the outer side of the heat generator 37. The protrusions 37*a* induce high-frequency plasma and prevent in-body tissues from be attached to the heat generator 37. That is, the protrusions 37*a* prevent tissues from sticking to the heat generator 37.

FIG. 3 is a partial cut perspective view showing the configuration of the high-frequency treatment 51 for a spinal endoscopic surgery according to a second embodiment of the present invention and FIG. 4 is a cross-sectional view showing the electrode tip of the high-frequency treatment for a spinal endoscopic surgery according to the second embodiment of the present invention.

The second embodiment of the present invention is particularly suitable for UBE, and in some cases, it may be applied to single-port spinal endoscopy.

As shown in the figures, another type of electrode tip 39 is fixed to the front end of the insert rod 29. The electrode tip 39 is a single part having holes 41*a*, a passage 41*b*, a seat 41*c*, and a shield 41*d* and is made of ceramic similar to the body 35 shown in FIG. 2.

The second embodiment of the present invention can be suitable for UBE with less limit in diameter of the electrode tip 39 and the insert rod 29, so it is possible to increase the size of the electrode tip 39, particularly, the heat generator 43 and it is possible to use the shield 41*d* that can prevent thermal conduction to roots.

The passage 41*d*, which is a way for suctioning objects that block the visual field around the electrode tip 41 in an operation, has the same function as the passage of the first embodiment.

The heat generator 43 made of tungsten is disposed on or in the seat 41*c*. The heat generator 43, as described above, generates heat by receiving high-frequency energy transmitted through the supply line 31 and outputs heat of 40° C. to 75° C. A plurality of protrusions 43*a* for inducing high-frequency plasma and preventing sticking of objects is also formed on the outer side of the heat generator 43.

The shield 41*d* shields in-body normal tissues from the heat generator 43 in an operation in order to prevent damage to roots by preventing thermal conduction to the roots. That is, the shield 41*d* prevents normal tissues from being thermally damaged by contacting the heat generator 43.

Further, the shape of the shield 41*d* may be changed in various ways in consideration of the size of the port that is used for UBE.

FIG. 5 is a view illustrating the entire configuration and operation of the high-frequency treatment device 51 for endoscopic spinal surgery according to the first embodiment of the present invention.

As shown in the figure, the high-frequency treatment device 51 for endoscopic spinal surgery according to the embodiment further includes a sensing unit 45 and a controller 47.

The sensing unit 45 measures in real time the temperature of in-body tissues heated by the electrode tips 33 and 39 and includes an out-body sensor 45*a* and an external sensor 45*b*.

The in-body sensor 45$a$ and out-body sensor 45$b$ may be selectively or both used in an operation.

The in-body sensor 45$a$, which is a temperature sensor that is directly put inside an operation part, directly checks the temperature of in-body tissues that are heated by the high-frequency treater. The information sensed by the in-body sensor 45$a$ is transmitted in real time to the controller 47.

The controller 47 receives the current temperature of the operation part from the in-body sensor 45$a$ and, when the temperature increases over an allowable level, that is, when there is a possibility of low-temperature burn of roots or tissues, the controller 47 stops the high-frequency output unit 22 through the switch unit 20.

Further, the out-body sensor 45$b$, which is a sensor that is fastened on a finger or a toe of a patient, senses fine convulsions of roots at the ends of a hand or a foot when excessive heat is applied to the spine and transmits the information to the controller 47. The controller 47 immediately stops the high-frequency output unit 22 through the switch 20 when receiving this information.

It is possible to inject cooling a saline solution to the operation part to cool the excessively heated part. The saline solution is injected to a target part in a body, that is, a treatment part or an operation part through the passage of an endoscope, and is then discharged through the passage 41$b$ of the electrode tips 33 and 39 after removing heat.

In general, an endoscope is inserted into a body through a separate cannula (not shown) and a saline solution is injected through an endoscope passage formed in the cannula. The injected saline solution removes the heat of heated roots or tissues and flushes out separated tissues, muscles, or pieces of bones or contaminated body fluid. The saline solution flushing out these substances is discharged with the substances out of the body.

Although the present invention was described in detail through a detailed embodiment, the present invention is not limited thereto and may be modified in various ways by those skilled in the art without departing from the spirit of the present invention.

What is claimed is:

1. A high-frequency treatment device for spinal endoscopic surgery, the high-frequency treatment device comprising:

a casing;

an insert rod extending in a longitudinal direction of the casing; and an electrode tip formed at a front end of the insert rod to apply heat to a treatment part, wherein the electrode tip includes:

a body fitted in the front end of the insert rod and having a passage that communicates with the insert rod, and a seat on a first side of the body; and a heat generator formed in the seat, the heat generator including a plurality of protrusions for preventing the heat generator and tissue of a human body from sticking to each other, and a plurality of holes that communicate with the passage of the body, wherein at least one of the plurality of holes is provided closer to the front end of the insert rod than any of the plurality of protrusions, wherein a shield for isolating the heat generator from a human tissue is further formed on a second side of the body, wherein a recess portion and a rim portion are provided on top of the shield, the recess portion being surrounded by the rim portion, heights of the rim and recess portion being lower than the seat, wherein the recess portion has a flat bottom that is lower than the rim portion.

2. The high-frequency treatment device of claim 1, wherein a seat for accommodating the heat generator is formed on the first side of the body, and the heat generator is disposed inside the seat and is operated with the protrusions exposed outside.

3. The high-frequency treatment device of claim 1, further comprising a discharge tube for discharging a saline solution to outside a human body through the holes, the passage, and the insert rod, wherein the saline solution has been injected to a treatment part in the human body.

4. The high-frequency treatment device of claim 1, wherein the casing has a trigger at a side to operate the electrode tip.

5. The high-frequency treatment device of claim 1, wherein the insert rod is formed in a hollow pipe coated with an insulating material on an outer side thereof.

6. The high-frequency treatment device of claim 1, wherein a high-frequency output unit operated to output high frequency waves by power supplied from the outside is disposed in the casing and energy generated by the high-frequency output unit is transmitted to the electrode tip.

7. The high-frequency treatment device of claim 6, wherein a switch unit operating the high-frequency output unit is further disposed in the casing, and the high-frequency treatment device further comprises:

a sensing unit determining suitability of temperature of tissues in a treatment part; and a controller turning on and off the switch unit in response to information sensed by the sensing unit, wherein the sensing unit and the controller are installed with the electrode tip.

8. The high-frequency treatment device of claim 7, wherein the sensing unit includes an in-body sensor inserted into a human body in an operation.

9. The high-frequency treatment device of claim 8, wherein the sensing unit includes an out-body sensor fastened on a finger or a toe of a patient to sense a nerve reaction of the finger or the toe.

* * * * *